United States Patent [19]

Payling et al.

[11] 4,356,181
[45] Oct. 26, 1982

[54] ANTI-ALLERGIC MONO SALT OF 6-METHYLAMINO-4-OXO-10-PROPYL-4H-PYRANO[3,2-g]-QUINOLINE-2,8-DICARBOXYLIC ACID

[75] Inventors: David W. Payling; John L. Suschitzky, both of Loughborough, England

[73] Assignee: Fisons Limited, London, England

[21] Appl. No.: 247,896

[22] Filed: Mar. 26, 1981

[30] Foreign Application Priority Data

Apr. 2, 1980 [GB] United Kingdom ................. 8011039

[51] Int. Cl.$^3$ ................... A61K 31/47; C07D 491/052
[52] U.S. Cl. ...................................... 424/258; 546/89
[58] Field of Search ........................... 546/89; 424/258

[56] References Cited

FOREIGN PATENT DOCUMENTS 2022078 12/1979 United Kingdom .

Primary Examiner—Richard A. Schwartz
Attorney, Agent, or Firm—Merriam, Marshall & Bicknell

[57] ABSTRACT

There is described the mono salt of 6-methylamino-4-oxo-10-propyl-4H-pyrano[3,2-g]-quinoline-2,8-dicarboxylic acid with a strongly basic cation.

There is also described an aqueous solution of 6-methylamino-4-oxo-10-propyl-4H-pyrano[3,2-g]quinoline-2,8-dicarboxylic acid the solution being at a pH of from 4 to 8.

The salts and solutions are useful as pharmaceuticals, e.g. in the treatment of allergies.

12 Claims, No Drawings

ANTI-ALLERGIC MONO SALT OF 6-METHYLAMINO-4-OXO-10-PROPYL-4H-PYRANO[3,2-g]-QUINOLINE-2,8-DICARBOXYLIC ACID

This invention relates to novel nitrogen heterocyclic compounds, methods for their production and pharmaceutical compositions containing them.

According to the invention we provide the pharmaceutically acceptable mono salt of 6-methylamino-4-oxo-10-propyl-4H-pyrano[3,2-g]-quinoline-2,8-dicarboxylic acid with a strongly basic cation.

The strongly basic cation is preferably an ammonium cation, a substituted ammonium cation, e.g. a mono- di- or tri-alkyl (preferably C 1 to 6) ammonium, such as a methyl ammonium, cation, an alkali metal cation, e.g. potassium, lithium or preferably a sodium cation, an alkaline earth metal cation, e.g. a calcium or magnesium cation, or an aluminium or zinc cation.

The mono salt may be made by conventional methods known per se, e.g. the reaction of the free acid 6-methylamino-4-oxo-10-propyl-4H-pyrano[3,2-g]-quinoline-2,8-dicarboxylic acid with the stoichiometric amount of an appropriate base followed by isolation of the product.

6-Methylamino-4-oxo-10-propyl-4H-pyrano[3,2-g]-quinoline-2,8-dicarboxylic acid contains two anion forming carboxylic acid groups and one cation forming heterocyclic N atom which is activated by the methyl amino group; and by the term 'mono salt' we mean the salt of the nett mono anionic species.

We have found that the di-salts of 6-methylamino-4-oxo-10-propyl-4H-pyrano[3,2-g]quinoline-2,8-dicarboxylic acid with strongly basic cations can produce strongly basic, potentially irritant and chemically unstable solutions on dissolution in water, e.g. body fluids. The mono-salts of the present invention produce solutions which are much more nearly neutral, and in consequence are more physiologically acceptable.

According to a further facet of our invention we provide an aqueous solution of 6-methylamino-4-oxo-10-propyl-4H-pyrano[3,2-g]quinoline-2,8-dicarboxylic acid the solution having at a pH of from 4 to 8, preferably from 4.5 to 7, and more preferably from 5.0 to 6.5.

The desired pH may be obtained by the addition of appropriate quantities of acid, base or other compounds. Preferably however the solution is buffered and suitable buffers include conventional pharmaceutically acceptable buffers producing the desired pH, e.g. phosphate and/or citrate buffers, such as a mixture of potassium dihydrogen phosphate and disodium hydrogen phosphate, or a mixture of disodium citrate and a suitable phosphate.

The compounds and compositions of the invention are useful because they possess pharmacological activity in animals; in particular they are useful because they inhibit the release and/or action of pharmacological mediators which result from the in vivo combination of certain types of antibody and specific antigen, e.g. the combination of reaginic antibody with specific antigen (see Example 27 of British Pat. No. 1,292,601). The compounds and compositions have also been found to inhibit the degranulation of mast cells and to interfere with reflex pathways in experimental animals and man, in particular those reflexes associated with lung function. In man, both subjective and objective changes which result from the inhalation of specific antigen by sensitised subjects are inhibited by prior administration of the new compounds and compositions. Thus the new compounds and compositions are useful in the treatment of reversible airway obstruction and/or to prevent the secretion of excess mucous. They are thus useful for the treatment of allergic asthma, so-called 'intrinsic' asthma (in which no sensitivity to extrinsic antigen can be demonstrated, e.g. exercise etc., induced asthma), farmer's lung, bird fancier's disease, bronchitis, coughs (including whooping cough) and the nasal and bronchial obstructions associated with the common cold. The new compounds and compositions are also of value in the treatment of other conditions in which antigen-antibody reactions or excess mucous secretion are responsible for, or are an adjunct to, disease.

For the above mentioned uses the dosage administered will, of course, vary with the compound or composition employed, the mode of administration and the treatment desired. However, in general, satisfactory results are obtained when the compounds are administered at a dosage of from 0.001 to 50 mg per kg of animal body weight in the test set out in Example 27 of British Pat. No. 1,292,601. For man the indicated total daily dosage is in the range of from 0.001 mg to 2,000 mg, preferably from 0.001 mg to 1,000 mg, more preferably from 0.01 mg to 200 mg and most preferably from 0.1 mg to 60 mg, which may be administered in divided doses from 1 to 6 times a day or in sustained release form. Thus unit dosage forms suitable for administration by inhalation or by swallowing comprise from 0.001 to 200 mg, preferably from 0.001 mg to 50 mg, more preferably from 0.01 mg to 20 mg and most preferably from 0.01 mg to 10 mg of the compound preferably admixed with a solid or liquid pharmaceutically acceptable diluent, carrier or adjuvant.

According to our invention we also provide a pharmaceutical composition comprising (preferably less than 80%, and more preferably less than 50% by weight of) a salt according to the invention in combination with a pharmaceutically acceptable adjuvant, diluent or carrier.

We particularly prefer the composition not to contain material capable of causing an adverse, e.g. an allergic, reaction in the patient. Materials which can cause adverse reactions are more fully described in Belgian Pat. No. 854,690.

Thus the new salts may be formulated in a manner suitable for application to the skin of the animal, e.g. as an ointment, cream, lotion, liniment, paste or gel.

When the new salts are to be used in aqueous solution or when a controlled pH solution is to be used we prefer the solution to be clear and to this end it may be necessary to make the solution with very pure water, e.g. containing very low amounts of dibasic, e.g. magnesium or calcium, ions, or to incorporate a chelating or sequestering agent in the solution. Aqueous solutions typically contain up to about 10% w/w of the new salt and may be used as drops or sprays.

When the new salts are to be used to treat the eye they may be used, for example, in the form of an aqueous solution, or an opthalmic ointment (e.g. in an oily base) or in a controlled release formulation, e.g. a device adapted to be inserted under the eyelid and to release the new compound at a controlled rate.

For oral or rectal administration the new salts may be worked up with inorganic or organic pharmaceutically acceptable adjuvants or excipients. Examples of such adjuvants are:

For tablets, lozenges and dragees: Binders, for example, cellulosic materials, e.g. microcrystalline cellulose and methyl cellulose; disintegrating agents, for examples starches, e.g. maize starch; stabilisers, e.g. against hydrolysis of the active ingredients; flavouring agents, for example sugars such as lactose; fillers e.g. microcrystalline cellulose or dicalcium phosphate; stearates and inorganic lubricants, e.g. talc or silica.

For syrups, suspensions, emulsions or dispersions: A liquid vehicle in which the active ingredients may be dissolved or suspended, e.g. water; and suspending agents, e.g. cellulose derivatives, gums etc.

For hard or soft capsules: Diluents, e.g. microcrystalline cellulose; glidants, e.g. stearates; inorganic materials, e.g. silica or talc; stabilisers and dispersing agents.

For suppositories: Natural or hardened oils, waxes etc. A large number of proprietary emulsifying bases are available and are suitable for use in suppositories. These include 'Witepsol' bases, consisting of hydrogenated triglycerides of lauric acid with added monoglycerides; and 'Massupol' bases, which consist of glyceryl monostearate.

For enemas: Water, sodium chloride, buffers etc, and optionally foam forming agents.

The composition may also contain further adjuvants, for example a composition for use in tablets may contain flow aids and glidants to assist in tabletting.

If desired the composition may be formulated in sustained release or film coated form.

For administration by inhalation the new salts may be formulated with a compressed gas, e.g. nitrogen, or a liquified propellant (such as propellant 11, 12, 114 or a mixture thereof) as a pressurised aerosol composition, the composition preferably containing from 1 to 20% w/w of the new salt. The composition also preferably contains less than about 5% w/w of water and more preferably is substantially anhydrous.

The composition may also contain a surface active agent, e.g. from 0.05 to 1.5% w/w of a liquid or solid non-ionic surface active agent or a solid anionic surface active agent.

For inhalation as a powder formulation the new salts in finely divided form may be used in admixture with a larger sized carrier comprising particles, e.g. of up to 400 microns diameter. We prefer the particles of the new salt to have a mass median diameter below 10 microns (and preferably of from 0.01 to 10 microns), and the carrier to have a mass median diameter below 400 microns, and preferably above 30 microns.

Alternatively, for inhalation the new salt may be used in pellet or granule form, wherein the pellet or granule is soft, is from 10 to 1,000, preferably 30 to 500, microns in diameter and comprises an agglomeration of individual medicament particles, at least 90% by weight of which have a diameter of less than 10 microns.

The soft pellet or granule preferably has an internal coherence such that the pellet or granule remains intact when filled into a container, e.g. a capsule, using automatic or semi-automatic filling machines, under conditions of transport and storage, and when fluidised within a container in the device from which it is intended to dispense the pellets or granules and yet may be broken up into particles of a therapeutically effective size outside the container as it discharges from the container.

Alternatively the new salt may be formulated for inhalation, opthalmic or intravenous administration as an aqueous solution, which can be sterlised by filtration, and in the case of multidose presentations may include a preservative, e.g. benzalkonium chloride.

The invention is illustrated, but in no way limited by the following Examples.

EXAMPLE 1

6-Methylamino-4-oxo-10-propyl-4H-pyrano[3,2-g]quinoline-2,8-dicarboxylic acid

(a) Dimethyl 1-(4-acetyl-3-hydroxy-2-propylphenyl) aminofumarate

4-Amino-2-hydroxy-3-propylacetophenone (19 g) and dimethyl acetylenedicarboxylate (14.5 mls; 16.8 g) in ethanol (200 mls) were refluxed for 7 hours. The solvent was removed by evaporation to give 36.4 g of the product as an oil. The structure was confirmed by NMR and MS.

(b) Methyl 6-acetyl-7-hydroxy-8-propyl-4-oxo-4H-quinoline-2-carboxylate

The product of step (a) (30 g) was added to diphenyl ether (300 mls) at reflux. The reaction mixture was refluxed for a further 5 mins after addition, cooled, and poured into a large volume of 60°–80° petroleum ether. The precipitated product was collected by filtration, washed with petroleum ether and dried to give 20 g of brown solid. A recrystallisation from a large volume of cyclohexane gave material having mp 169°–170°.

(c) Methyl 6-acetyl-4-chloro-7-hydroxy-8-propylquinoline-2-carboxylate

The product of step (b) (3 g, 0.0099 mole) was dissolved in dry benzene (50 mls), treated with phosphoryl chloride (2.5 mls) and refluxed for 1 hour. The reaction mixture was cooled, poured into water and extracted with ether, which was then washed with water and dried over magnesium sulphate. The solvent was evaporated to leave 2.8 g of yellow-brown solid. Recrystallisation from cyclohexane gave yellow needles mp 163°–164°.

(d) 6-Acetyl-7-hydroxy-4-methylamino-8-propylquinoline-2-carboxylic acid

The product of step (c) (8.9 g) was treated with 33% w/w methylamine in ethanol (100 mls) and heated in an autoclave at 100° C. for 17 hours. The reaction mixture was cooled and poured into a mixture of water and ethyl acetate. The organic layer was separated, washed with water and dried over magnesium sulphate. The solvent was evaporated to leave 9.0 g of N-methyl-7-hydroxy-4-methylamino-6-[(1-methyl-imino)ethyl]-8-propyl-quinoline-2-carboxamide.

The amide (7.0 g) was treated with 70% sulphuric acid (350 mls) and heated under reflux for 45 mins. The reaction mixture was cooled and aqueous ammonia added with ice cooling until pH 7 was reached. The gelatinous product was collected by filtration, washed well with water and dried to give 6.4 g of the sub-title compound.

(e) Ethyl 6-acetyl-7-hydroxy-4-methylamino-8-propylquinoline-2-carboxylate

The crude product of step (d) (6.4 g) in ethanol (500 mls) which had been previously saturated with hydrogen chloride gas was heated under reflux for 1 hour. The reaction mixture was cooled, made basic with conc. aqueous ammonia solution and extracted with ethyl acetate, which was then washed with water and dried over magnesium sulphate. The solvent was removed by evaporation to leave 8.0 g of residual yellow solid. This solid was recrystallised from ethanol to give 3.8 g of yellow needles mp 219°–220°.

(f) Diethyl 6-methylamino-4-oxo-10-propyl-4H-pyrano[3,2-g]quinoline-2,8-dicarboxylate The product of step (e) (3.6 g) and diethyl oxalate (14 g) dissolved in dry dimethylformamide (150 mls) was added to ether washed 50% sodium hydride in oil (2.3 g) suspended in dry dimethylformamide (120 mls) under nitrogen with stirring. The reaction mixture was stirred for 24 hours and then poured into water, acidified with glacial acetic acid and extracted with ethyl acetate which was then washed with water and dried. The solvent was evaporated to leave an oil which was dissolved in ethanol (300 mls), which had previously been saturated with hydrogen chloride gas, and then refluxed for 15 mins. The reaction mixture was cooled, made basic with conc. aqueous ammonia solution and the precipitated solid collected by filtration, washed with water and dried to give 4.1 g of product. A recrystallisation from ethanol gave 2.9 g of crystalline product mp 235°–237°.

(g) 6-Methylamino-4-oxo-10-propyl-4H-pyrano[3,2-g]quinoline-2,8-dicarboxylic acid, monosodium salt Diethyl 6-methylamino-4-oxo-10-propyl-4H-pyrano[3,2-g]quinoline-2,8-dicarboxylate (1.932 g) in methanol (200 ml) was heated at reflux with stirring and N NaOH solution (9.38 ml) was added dropwise.

The reaction mixture was stirred under reflux for 2 hours, then cooled and filtered. The solvent was removed in vacuo, and the residue was taken up in water (100 ml) and diluted with acetone. The precipitate was collected and stirred with 2 N HCl solution (20 ml) for 2 hours. Filtration afforded the di-acid as a yellow solid (0.606 g).

The solid (0.5706 g) was treated with sodium bicarbonate (0.1242 g) in water (20 ml) for 2 hours, and the water was removed by lyophilisation to afford the subtitle compound (0.6 g).

NMR:
$\delta$DMSO: 1.0(3H,t), 1.8(2H,m), 3.0(3H,d), 3.6(2H,t), 6.8(7H,s), 7.0(7H,s), 8.5(7H,d), 9.0(7H,s).

EXAMPLE 2
(Buffered solution)

Disodium hydrogen phosphate dihydrate (10.92 g) and potassium dihydrogen phosphate (9.80 g) were dissolved in sufficient distilled water to give 2 liters of a solution of pH 6.5.

Sufficient disodium 6-methylamino-4-oxo-10-propyl-4H-pyrano[3,2-g]quinoline-2,8-dicarboxylate was dissolved in the above solution to give a concentration of 0.5% w/v, without changing the pH of the solution substantially.

EXAMPLE A
Pharmaceutical Formulations

| (a) Topical | % w/w |
|---|---|
| 1. Oil in water cream | |
| Arlacel 165 | 10 |
| White soft paraffin | 10 |
| Isopropyl myristate | 5 |
| Stearic acid | 5 |
| Sorbitol solution | 5 |
| Compound of Example 1 (g) | 0.5 |
| Preservative | q.s e.g. 0.2% |
| Distilled water | to 100 |
| 2. Gel | |
| Compound of Example 1 (g) | 1.0% w/w |
| Carbomer BP | 2.5 |
| Propylene glycol | 28.0 |
| Sodium hydroxide | 0.45 |
| Distilled water | to 100 |

This composition may be packaged in an internally lacquered aluminium tube fitted with a lined screw cap and folded and crimped at one end.

| (b) Rectal | |
|---|---|
| 3. Suppository | |
| Compound of Example 1 (g) | 10% w/w |
| 'Macrogol' 4000 | 30 |
| 'Macrogol' 6000 | 43 |
| Distilled water | to 100 |

This composition may be packaged in a plastic strip pack.

| (c) Tablets/capsules | mg/tablet |
|---|---|
| (i) Compound of Example 1 (g) (150 micron) | 20.0 |
| Microcrystalline cellulose BPC | 170.5 |
| Cross linked sodiumcarboxymethylcellulose | 2.0 |
| Polyvinylpyrrolidone | 4.0 |
| Magnesium stearate | 2.0 |
| Colloidal silica | 1.5 |
| | 200.0 |

The finely ground drug is dry mixed with the excipients (excluding magnesium stearate) for 20 minutes, the magnesium stearate added, then mixing continued for a further 5 minutes. The final mixture is then compressed on 8.5 mm diameter normal concave punches to a diametral crushing of 5–7 kp Schleuniger.

| | mg/capsule |
|---|---|
| (ii) Compound of Example 1 (g) | 20 |
| Microcrystalline cellulose | 98 |
| Sodiumcarboxymethylcellulose | 1 |
| Magnesium stearate | 0.5 |
| Colloidal silica | 0.5 |
| | 120.0 |

The powders are dry mixed in a similar manner to (i) above, and the final mixture filled on a capsule machine into Size 2 hard gelatin capsule shells.

The tablets or capsules may be loose filled into internally lacquered aluminum cans or packed in a polyvinylidene chloride/aluminum foil blister overwrapped with an aluminum foil.

| (d) Lozenges | mg/lozenge |
|---|---|
| Compound of Example 1 (g) (micronised) | 10 |
| Sugar, pulverised BP (1968) | 765 |
| Stearic acid BPC intragranule | 6.00 |
| extragranule | 5.40 |
| Menthol BP | 0.62 |
| Eucalyptus Oil BP | 1.80 |
| Oil of Lemon, Terpeneless BPC | 0.18 |
| Granulating Solution: | |
| Liquid Glucose BPC | 5.50 |
| Gelatin BP | 5.50 |
| | 800.00 |

The drug, sugar and intragranule stearic acid are mixed, then moistened with an aqueous solution containing 10% w/w liquid glucose, 10% w/w gelatin. The moistened mass is passed through a 1000 micrometer screen, dried at 60° C. and re-passed through a 1000 micrometer screen. The menthol is dissolved in a mixture of eucalyptus oil and lemon oil and mixed for 10 minutes with about 10% of the dry granules. These mixed granules are added with the extragranule stearic acid to the remaining granules and mixed for a further 5 minutes. The product is then compressed on a 12 mm diameter flat-faced, bevelled edge punches in a tablet machine to a diametral crushing strength of >7 kg Schleuniger.

The lozenges may be roll wrapped with an aluminum foil laminate and packed into aluminum tubes.

| (e) Brushable paste | % w/w |
|---|---|
| Compound of Example 1 (g) | 4 |
| Sodium Carboxymethylcellulose | 1.5 |
| Glycerol | 25 |
| Nipastat | 0.1 |
| Propylene glycol | 0.4 |
| Sodium saccharin | 0.1 |
| Water | 25.2 |
| Sodium lauryl sulphate | 2 |
| Dicalcium phosphate dihydrate | 41 |
| Flavour | 0.7 |

The Nipastat is dispersed in the propylene glycol and heated to 50° C. with the glycerol. The sodium carboxymethylcellulose is added with rapid stirring to aid dispersion, and the water containing the dissolved drug then added while slowly stirring. Stirring is continued for 20 minutes until the components are fully dispersed, maintaining the vessel at 50° C. throughout, and a vacuum then applied to deaerate the dispersion while stirring is continued for a further 10 minutes. The dicalcium phosphate dihydrate is mixed in under vacuum, and finally, sodium lauryl sulphate and flavour are similarly mixed in before cooling the contents to 25°–30° C. before filling the paste into, e.g. epoxy lacquered aluminum tubes or other containers.

| (f) Intravenous or eye drop formulation | |
|---|---|
| Compound of Example 1 (g) | 0.50 g |
| Sodium chloride | 0.84 g |
| Water for injection (low metals) | to 100 ml |

Sterilisation is achieved by filtration. Intravenous solutions are prepared using aseptic conditions and pyrogen and particle free water or saline.

| (g) Inhalation powder formulation | Weight per capsule | % w/w |
|---|---|---|
| (a) lung (for inhalation) | | |
| Compound of Example 1 (g) (micronised) | 5 mg* | 12.5* |
| Classified lactose (substantially 30 to 80 microns) | q.s. ad 40 mg | q.s. ad 100.0 |
| (b) nose (for insufflation) | | |
| Compound of Example 1 (g) (micronised) | 2.5 mg* | 12.5* |
| Classified lactose (substantially 30 to 80 microns) | q.s. ad 20 mg | q.s. ad 100.0 |

*As anhydrous material

Use one capsule for each nostril

METHOD

Place half of the lactose in a suitable mixer and add the micronised drug. Add the remaining lactose and mix until homogeneous. Fill into No 2 hard gelatin capsules using either automatic or semiautomatic filling machines.

| (i) Aerosol formulation (cold fill) | % w/w |
|---|---|
| Compound of Example 1 (g) (micronised) | 2.8839* |
| Sorbitan trioleate | 0.5047 |
| Propellent 114 | 38.6446 |
| Propellent 12 | 57.9668 |

*As anhydrous material

METHOD

Cool the propellant 12° to −55° C. and disperse the sorbitan trioleate in it using a high-shear mixer. Disperse the drug in this mix and finally add the propellant 114, at −55° C. Fill into suitable cans while still cold, fit a metering valve and crimp.

| (j) Aerosol formulation (concentrate/pressure fill) | % w/w |
|---|---|
| (i) Concentrate | |
| Compound of Example 1 (g) (micronised) | 6.9009 |
| Dioctyl Sodium Sulphosuccinate | 0.2393 |
| Propellent 114 | 92.8598 |

METHOD

Cool the propellant 114 to 0° C. and dissolve in it the dioctyl sodium sulphosuccinate. Add the micronised drug and disperse using a high-shear mixer. Maintain at 0° C.

| (ii) Cans | Weight per can |
|---|---|
| Concentrate | 6.81 g |
| Propellent 12 | 9.49 g |

METHOD

Dispense the concentrate at 0° C. into the cans and seal each by crimping on a suitable metering valve. Pressure fill the required quantity of propellant 12 into each can.

EXAMPLE B

Clinical evaluation of the salts and solutions of the invention may be carried out using the antigen inhalation provocation test described:

The human volunteer selected for test purposes suffers from specific allergic asthma. In this subject an asthma attack normally follows the inhalation of an antigen to which he is specifically sensitive. The degree of asthma provoked by this method can be measured by repeated examination of the air way resistance.

A suitably designed spirometer is used to measure the forced expiratory volume at one second ($FEV_{1.0}$) hence the changes in air way resistance. In each instance equivalent doses of an 0.5% aqueous solution of the drug are administered by inhalation for 1 minute.

Drug induced changes in $FEV_{1.0}$ are measured at 5 minutes after administration of the drug.

Six hours after drug administration a standard antigen challenge is administered to the human volunteer and the fall in $FEV_{1.0}$ measured at 5 minutes after the antigen administration.

The results of these tests show that the percentage fall in $FEV_{1.0}$ 5 minutes after drug administration (a measure of drug induced bronchoconstriction) is more than twice as great with the solution of the disodium salt of 6-methylamino-4-oxo-10-propyl-4H-pyrano[3,2-g]-quinoline-2,8-dicarboxylic acid in water as with the buffered solution of Example 2. Furthermore the buffered solution gave 50% greater protection than the unbuffered solution in the antigen challenge test set out above.

EXAMPLE C (stability)

(a) In exactly comparable (0.057%) solutions of respectively the mono- and di-sodium salts of 6-methylamino-4-oxo-10-propyl-4H-pyrano[3,2-g]-quinoline-2,8-dicarboxylic acid in water held at 37° in the dark for one week it was found by means of reverse phase high pressure liquid chromatography that at least 6 times more of the di-sodium salt had been degraded as compared to the mono-sodium salt.

(b) 0.057% Aqueous solutions of 6-methylamino-4-oxo-10-propyl-4H-pyrano[3,2-g]-quinoline-2,8-dicarboxylic acid held at pH 5.27, 6.11 and 7.13 at 37° C. showed no loss of drug after 7 days. Exactly comparable solutions held at pH 9.63 and 11.2 respectively contained 6.2% after 7 days and 1% after 24 hours respectively of the original drug.

We claim:

1. A mono salt of 6-methylamino-4-oxo-10-propyl-4H-pyrano[3,2-g]-quinoline-2,8-dicarboxylic acid with a strongly basic pharmaceutically acceptable cation.

2. A salt according to claim 1, wherein the cation is an alkali metal cation.

3. A salt according to claim 2 which is 6-methylamino-4-oxo-10-propyl-4H-pyrano[3,2-g]quinoline-2,8-dicarboxylic acid, monosodium salt.

4. An aqueous solution of a mono salt according to claim 1, the solution having a pH of from 4 to 8.

5. A solution according to claim 4 having a pH of 4.5 to 7.

6. A solution according to claim 5 having a pH of 5.0 to 6.5.

7. A solution according to claim 4 which is a buffered solution.

8. A pharmaceutical composition useful for treatment of reversible airway obstruction or for prevention of the excretion of excess mucous comprising an effective amount of a salt according to claim 1 and a pharmaceutically acceptable excipient, diluent or carrier.

9. A composition according to claim 8 in a form suitable for administration by inhalation.

10. A composition according to claim 8 comprising from 0.001 to 200 mg of a salt according to claim 1 in unit dosage form.

11. A method of treatment of reversible airway obstruction or of prevention of the excretion of excess mucous which comprises administering an effective amount of a salt according to claim 1 to an individual suffering or liable to suffer from such a condition.

12. A method of treatment of reversible airway obstruction or of prevention of the excretion of excess mucous which comprises administering an effective amount of a solution according to claim 4 to an individual suffering or liable to suffer from such a condition.

* * * * *

Disclaimer 4,356,181.—*David W. Payling* and *John L. Suschitzky,* Loughborough, United Kingdom. ANTI-ALLERGIC MONO SALT OF 6-METHYL-AMINO-4-OXO-10-PROPYL-4H-PYRANO [3,2-]-QUINOLINE-2,8-DICARBOXYLIC ACID. Patent dated Oct. 26, 1982. Disclaimer filed Apr. 22, 1983, by the assignee, *Fisons Ltd.*

Hereby enters this disclaimer to claims 1-12 of said patent.
[*Official Gazette June 7, 1983.*]